United States Patent

L'vov

Patent Number: 5,315,528
Date of Patent: May 24, 1994

[54] METHOD OF, AND APPARATUS FOR, ABSORBANCE CORRECTION IN ATOMIC ABSORPTION SPECTROSCOPY

[75] Inventor: Boris V. L'vov, Leningrad, U.S.S.R.

[73] Assignee: The Perkin-Elmer Corporation, Norwalk, Conn.

[21] Appl. No.: 801,990

[22] Filed: Dec. 3, 1991

[51] Int. Cl.⁵ .................................. G01J 3/00
[52] U.S. Cl. .................... 364/498; 356/307; 356/315
[58] Field of Search ............... 364/498; 356/307, 312, 356/315, 311

[56] References Cited

U.S. PATENT DOCUMENTS

| | | | |
|---|---|---|---|
| 4,300,833 | 11/1981 | Harnly et al. | 356/312 |
| 4,449,820 | 5/1984 | Koizumi et al. | 356/307 |
| 4,457,623 | 6/1984 | Bohler et al. | 356/307 |
| 4,620,284 | 10/1986 | Schnell et al. | 364/498 |
| 4,895,443 | 1/1990 | de Loos-Vollebregt et al. | 356/312 |
| 5,080,485 | 1/1992 | Sperling | 356/315 |
| 5,094,530 | 3/1992 | Rogasch et al. | 356/307 |
| 5,118,187 | 6/1992 | Tamm et al. | 356/312 |

FOREIGN PATENT DOCUMENTS

| | | |
|---|---|---|
| 0384337 | 2/1990 | European Pat. Off. |
| 1325307 | 7/1987 | U.S.S.R. |

OTHER PUBLICATIONS

Holcombe et al. "Atomic Absorption, Atomic Emission, and Flame Emission", Analytical Chemistry, Jun. 15, 1990, pp. 169R–184 R.

Jackson et al. "Atomic Absorption, Atomic Emission, and Flame Emission", Analytical Chemistry, Jun. 15, 1992, pp. 50R–66R.

*Primary Examiner*—Thomas G. Black
*Assistant Examiner*—Tan Q. Nguyen
*Attorney, Agent, or Firm*—Edwin T. Grimes

[57] ABSTRACT

In order to provide a linear calibration graph when analysing samples by atomic absorption spectroscopy, a maximum absorbance value is determined conventionally for a given analyte. The individual absorbance values of a sample containing an unknown amount of the analyte are processed as a function of the maximum absorbance value in accordance with the function $$A_o^* = (1 - 10^{-A_{max}}) \log \frac{10^{A_{max}} - 1}{10^{A_{max}-A} - 1}$$

The thus obtained corrected individual absorbance values are integrated with respect to time to yield a corrected time-integrated absorbance value which is proportional to the amount of analyte present in the sample. This amount is determined using a calibration factor obtained from the analogously corrected time-integrated absorbance value of a calibration sample containing a known amount of the analyte.

23 Claims, 10 Drawing Sheets

METHOD OF, AND APPARATUS FOR, ABSORBANCE CORRECTION IN ATOMIC ABSORPTION SPECTROSCOPY

The present invention generally relates to a method of, and apparatus for, determining by atomic absorption spectroscopy the amount of an analyte contained in a sample.

BACKGROUND OF THE INVENTION

In atomic absorption spectroscopy a line emitting light source such as a hollow cathode lamp emits a measuring light beam containing a resonance line of an analyte the amount of which in a sample is to be determined. The sample is introduced into an atomizer and atomized therein such that the sample forms an atomic vapor in which the analyte contained in the sample exists in the atomic state. The measuring light beam passes through this atomic vapor and impinges upon a photoelectric detector. The measuring light beam is attenuated by the atomic vapor as a function of the number of atoms of the analyte which are contained in this atomic vapor and absorb the resonance line.

The atomizer may be a flame produced by a burner. In this case, a solution of the sample is continuously sprayed into a mixing chamber of the burner by means of a nebulizer for producing a continuous absorption signal.

The atomizer instead may be an electrothermal atomizer such as a graphite tube atomizer. A metered quantity of sample is introduced into the electrothermal atomizer and atomization is effected by passing a strong current through the electrothermal atomizer. The atomizer is thereby heated to atomization temperature and atomizes the sample. There is thus obtained a transient, peak-shaped signal.

In any case, the detector generates a signal which is indicative of the amount of the analyte contained in the sample. This detector output signal can be calibrated in terms of, for example, "concentration" in the case of the flame atomizer, or "quantity" in the case of the electrothermal atomizer. In the latter case, the transient signal is usually integrated with respect to time and this time-integrated signal is used for determining the quantity of the analyte contained in the sample.

In order to correct for "background absorption" due to, for example, absorption by non-atomized molecules in the atomic vapor, it is known to apply a magnetic field to the atomic vapor. Because of the Zeeman effect, the resonance lines of the atoms in the atomic vapor, then, are shifted and the resonance line of the measuring beam is no longer absorbed. Thus, in the presence of the magnetic field, there will be no specific absorption of the measuring beam by the atoms of the analyte and only the background absorption is measured. In the absence of the magnetic field, both the specific absorption and the background absorption become effective to attenuate the resonance line of the measuring beam. A signal indicative of specific absorption alone and corrected for background absorption can thus be obtained by simple arithmetic.

For quantitative determination, the instrument has to be calibrated. Samples containing known amounts of the analyte are supplied to the atomizer. Theoretically, the absorption to which the measuring beam is subjected, should follow Lambert-Beer's law: The logarithm of the detected light intensity in the presence of the analyte referenced to the unattenuated light intensity or, if desired, referenced to the detected light intensity attenuated by a blank, i.e. the absorbance, is proportional to the number of atoms of the analyte in the atomic vapor. Thus, if the absorbance is plotted versus the amount of the analyte contained in the sample, a linear graph passing through the origin ought to be obtained. From such graph, the amount of the analyte contained in the sample can be determined. It has been found, however, that frequently and particularly so during use of the electrothermal atomizer, the graph of the absorbance versus the amount of the analyte is non-linear. Specifically, the graph is increasingly curved at high amounts of the analyte in the sample and asymptotically approaches a maximum absorbance value in non-Zeeman measurements. When utilizing the aforenoted Zeeman background correction, the graph even passes through a maximum and drops again at still larger amounts of the analyte (roll-over).

Therefore, it is one object of the invention to provide a method and apparatus of the initially mentioned type and which method and apparatus permit obtaining substantial linearization of the measured absorbance as a function of the analyte quantity so that the obtained signal is substantially proportional to the analyte quantity substantially through entire range of measurement.

It is a further and highly important object of the invention to provide a method and an apparatus of the initially mentioned type and which method and apparatus permit obtaining substantially linearized calibration graphs particularly but not exclusively through substantially the entire measurement range of time-integrated absorbance using electrothermal atomizers in the absence as well as in the presence of Zeeman background correction.

SUMMARY OF THE INVENTION

In order to implement these and other objects of the invention, the inventive method of determining by atomic absorption the amount of an analyte in a sample, according to one aspect of the invention, is manifested by comprising, among other steps, the steps of electrothermally atomizing a predetermined number of samples containing known amounts of an analyte and integrating with respect to time the respectively obtained transient atomic absorption signals, thereby determining a maximum absorbance value. Thereafter a sample containing an unknown amount of the analyte is atomized in order to obtain a transient atomic absorption signal composed of individual absorbance values as a function of time. The individual absorbance values are evaluated as a function of the maximum absorbance value for obtaining corrected individual absorbance values.

The corrected individual absorbance values are integrated with respect to time in order to produce a corrected time-integrated absorbance value which is proportional to the unknown amount of analyte contained in the sample. A calibration factor is determined and then the unknown amount of the analyte which is contained in the sample, is determined from the corrected time-integrated absorbance value and the calibration factor.

In accordance with a preferred embodiment of the invention, I have found that the curvature of a non-linear calibration graph can be explained by stray light or by a phenomenon having the nature of stray light, i.e. light which is not absorbed by the atomic vapor. This means that, at the detector, the refence intensity $I_o$ and the measured intensity I detected in the presence of the atomic vapor of the sample have superimposed thereon an intensity $\alpha I_o$ which is proportional to the reference intensity $I_o$. Thus, the logarithm of the ratio of these intensities, which ratio is formed in atomic absorption spectroscopy, is $$A = \log \frac{I_o + \alpha I_o}{I + \alpha I_o} \tag{1}$$

and obtained instead of $\log I_o/I$. Setting $$\log I_o/I = A_o, \tag{2}$$

equation (1) can be solved for $A_o$ and yields $$A_o = \log \frac{10^A}{1 + \alpha(1 - 10^A)}. \tag{3}$$

The maximum absorbance value is obtained from equation (1) for I→0. This yields $$A_{max} = \log \frac{1 + \alpha}{\alpha} \tag{4}$$

or $$\alpha = \frac{1}{10^{A_{max}} - 1}. \tag{5}$$

Thus, $A_{max}$ is determined from the non-linear calibration curve of the analyte and $A_o$ is derived from a measurement of A in accordance with equation (3). $A_o$ is a linear function of the amount of analyte which is contained in the sample. If $A_o$ (as computed in accordance with equation (3) from the measured value of A) were plotted as a function of the amount of analyte contained in the sample, a substantially linear graph passing through the origin would be obtained. However, the slope of this graph would differ from the correct slope. Therefore, correction is required by a normalization factor $1/(1+\alpha)$ or $$(1 - 10^{-A_{max}}). \tag{6}$$

The normalized absorbance $A_o^*$ due to the absorption of the measuring light beam by the atoms of the analyte in the atomic vapor formed by the atomized unknown sample, therefore, is given by the equation $$A_o^* = (1 - 10^{-A_{max}})\log \frac{10^{A_{max}} - 1}{10^{A_{max}-A} - 1}. \tag{7}$$

Thus the determination of the amount of the analyte contained in the sample in the preferred embodiment relies upon evaluating the aforementioned individual absorbance values in terms of equation (7) and determining, from the thus obtained $A_o^*$ values, a corrected time-integrated absorbance value which is proportional to the analyte amount contained in the sample. The amount of the analyte contained in the sample is, then, obtained by applying the calibration factor.

According to an other aspect of the invention, the apparatus for determining by atomic absorption spectroscopy the amount of an analyte contained in a sample, among other things, comprises line emitting light source means for emitting a measuring light beam which contains a resonance line of an analyte contained in the sample. Further provided is electrothermal atomizing means defining an atomic vapor area in which the received sample is atomized. The electrothermal atomizing means are arranged such that the measuring light beam passes through the atomic vapor area. Detector means follow the electrothermal atomizing means and modulating means provide that alternatingly the measuring light beam is passed through the atomic vapor area to the detector means and to the detector means. As a result, alternating detector output signals are produced which are indicative of the attenuated light intensity due to passage of the measuring light beam through the atomic vapor area and of a reference light intensity. Such alternating detector output signals are received by logarithmating means which generate therefrom a logarithmic ratio signal representative of an absorbance value. The atomized samples are transiently formed in the atomic vapor area and, therefore, the logarithmating means generate individual absorbance values as a function of time. Integrating means are selectively connected to the logarithmating means for forming time-integrated absorbance values. First memory means are connected to the integrating means for storing a maximum absorbance value obtained from a sample containing a predetermined high amount of the analyte. First applying means selectively connect the logarithmating means either to the integrating means or to programmable computing means in order to respectively store the maximum absorbance value or evaluate individual absorbance values obtained from a sample containing an unknown amount of the analyte as a function of the maximum absorbance value. The thus obtained corrected individual absorbance values are integrated by the integrating means in order to thereby form a corrected time-integrated absorbance value proportional to the unknown amount of the analyte contained in the sample. This corrected value is, then, converted by means of a calibration factor generated by calibrating means into an output signal indicative of the amount of analyte to be determined.

In a variant of the inventive method and apparatus, a peak height absorbance value is determined using any appropriate type of atomizing means. Such peak height absorbance value can also be corrected on the basis of a maximum absorbance value in corresponding manner which likewise results in a corrected peak height absorbance value which is proportional to the amount of the analyte to be determined in a sample.

DETAILED DESCRIPTION OF THE PREFERRED EMBODIMENTS

Figure 1:
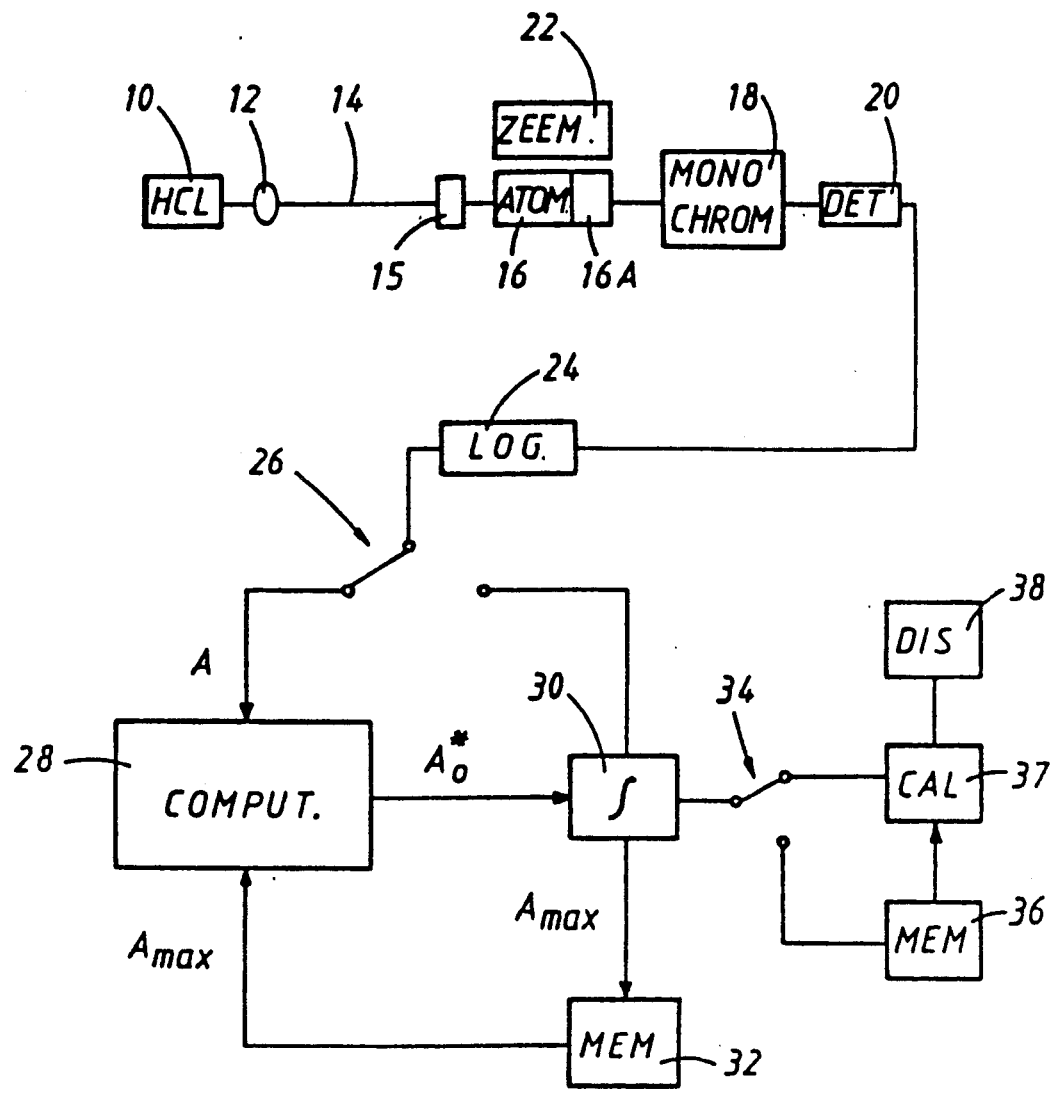
FIG. 1 is a block diagram illustrating a first exemplary embodiment of the inventive atomic absorption spectrophotometer.

FIG. 1 is a block diagram illustrating a first exemplary embodiment of the inventive atomic absorption spectrophotometer. Reference numeral 10 designates a hollow cathode lamp which emits a line spectrum containing the resonance lines of an element which is to be determined in a sample. The light from the hollow cathode lamp 10 is focused by an optical system 12 to form a measuring light beam 14. The optical system 12 is symbolized by a lens. The hollow cathode lamp 10 and the focusing optical system 12 represent "line emitting light source means". The measuring light beam 14 passes through electrothermal atomizing means 16 which may constitute, for example, a graphite tube atomizer. When a sample is introduced into the electrothermal atomizing means 16, an analyte contained in the sample is atomized and present in its atomic state in an atomic vapor area which is schematically indicated at 16A. In the case of a graphite tube furnace, this atomic vapor area is constituted by the bore of the graphite tube.

The measuring light beam 14 is subject to absorption by the atoms of the analyte present in the atomic vapor area 16A. Then, the measuring light beam 14 passes through a monochromator 18 and finally impinges upon detector means 20 such as, for example, a photomultiplier.

Modulating means 15 like, for example, a chopper are provided for alternatingly directing the measuring light beam 14 through the electrothermal atomizing means 16 and past the same so that the detector means 20 alternatingly receives the measuring light beam 14 with an intensity I, which is attenuated by the atoms of the analyte present in the atomic vapor area 16A, and with an unattenuated intensity $I_o$ which serves as a reference light intensity. If desired, there can additionally be provided base line correction means (not illustrated).

Further, conventional Zeeman background correction means 22 can be optionally associated with either the hollow cathode lamp 10 or the electrothermal atomizing means 16, as the case may be.

The detector means 20 is connected to logarithmating means 24 which receive alternating detector output signals corresponding to the aforementioned alternating attenuated und unattenuated intensities I and $I_o$ of the measuring light beam 14. The logarithmating means 24 transforms the incoming alternating detector output signals into a logarithmic ratio signal representative of the momentary value of absorbance log $I_o/I$.

The logarithmating means 24 are connected on their output side to applying means 26 for selectively applying the logarithmic ratio signal to either one of programmable computing means 28 or integrating means 30. The integrating means 30 serve to integrate the applied logarithmic ratio signal with respect to time and are connected to first memory means 32 for storing a thus obtained time-integrated absorbance value. The first memory means 32, in turn, is connected to the programmable computing means 28 for providing therein the stored time-integrated absorbance value and may also constitute part of such programmable computing means 28. Also, the programmable computing means 28 may be part of or integrated with a central data processing and control unit of the atomic absorption spectrophotometer.

The programmable computing means 28 processes the incoming data in accordance with a manner described further herein-below. The processed data are outputted and fed through the integrating means 30 to second applying means 34 which serve to selectively connect the integrating means 30 to either one of second memory means 36 or calibrating means 37. The second memory means 36 serve to store a time-integrated absorbance value obtained from a standard sample. The calibrating means 37 serve to generate a calibration factor on the basis of the stored time-integrated absorbance value obtained from the standard sample and to multiply the calibration factor and the time-integrated absorbance value obtained from a sample containing an unknown amount of the analyte. There is thus determined the amount of the analyte present in the sample in suitably selected units like, for example, mass or concentration units and this result is indicated at a display unit 38 such as a recorder, screen or the like.

The aforedescribed atomic absorption spectrophotometer is operated in accordance with the inventive method as follows:

In the presence of the Zeeman background correction means 22, the conventional calibration curve showing the absorbance A as a function of the amount or quantity of the analyte, which is contained in the sample, passes through a maximum (roll-over) absorbance value. In the absence of the Zeeman background correction means 22, the absorbance asymptotically approaches a maximum absorption value. Therefore, depending upon the presence or absence of the Zeeman background correction means 22, the following procedure is adopted:

In the presence of the Zeeman background correction means 22, a number of samples containing the analyte to be determined, is introduced into the electrothermal atomizing means 16. The amount of the analyte is selected in a range in which the absorbance value passes through a maximum. The first applying means 26 is adjusted for connecting the logarithmating means 24 to the integrating means 30 and the time-integrated absorbance value associated with the maximum of the calibration curve, is selected and stored in the first memory means 32 as the maximum absorbance value $A_{max}$.

In the absence of the Zeeman background correction means 22, there is used a sample which contains the analyte to be determined in a high amount in the range in which the absorbance value changes only little as a function of the amount of the analyte. The first applying means 26 is adjusted for connecting the logarithmating means 24 to the memory means 30 and the absorbance value thus obtained is stored in the first memory means 32 as the maximum absorbance value $A_{max}$.

Then, the first applying means 26 is switched for connecting the logarithmating means 24 to the programmable computing means 28 and the second applying means 34 is adjusted such as to interconnect the integrating means 30 and the second memory means 36. A calibration sample containing a known amount of the analyte to be determined, is introduced into and atomized in the electrothermal atomizing means 16. The programmable computing means 28, then, receives a flow of individual absorbance values A as a function of time in correspondence with the transient atomic absorption signal appearing at the output of the detector means 20. The programmable computing means 28 is programmed to correct the received individual absorbance values as a function of the maximum absorbance value $A_{max}$, most preferably in accordance with the function $$A_o^* = (1 - 10^{-Amax})\log \frac{10^{Amax} - 1}{10^{Amax-A} - 1}$$

as given in equation (7) hereinabove. The thus obtained corrected individual absorbance values $A_o^*$ are integrated with respect to time by the integrating means 30 and the corrected time-integrated absorbance value is stored in the second memory means 36.

Thereafter, the second applying means 34 is switched for connecting the integrating means 30 to the calibrating means 37. The stored corrected time-integrated absorbance value, which is associated with the calibration sample and present in the second memory means 36, is transferred to the calibrating means 37 which forms a calibration factor on the basis of the corrected time-integrated absorbance value and the known amount of the analyte contained in the calibration sample. A sample containing an unknown amount of the analyte, is introduced into and atomized in the electrothermal atomizing means 16. The programmable computing means 28, then, receive a flow of individual absorbance values A as a function of time in correspondence with the transient atomic absorption signal appearing at the output of the detector means 20. As mentioned hereinbefore, the programmable computing means 28 processes the incoming individual absorbance values A to correct the same as a function of the maximum absorbance value $A_{max}$ which is transferred from the first memory means 32, most preferably in accordance with the function $$A_o^* = (1 - 10^{-Amax})\log \frac{10^{Amax} - 1}{10^{Amax-A} - 1}$$

as given in equation (7) hereinabove. The thus obtained corrected individual absorbance values $A_o^*$ are integrated with respect to time by the integrating means 30 and the corrected time-integrated absorbance value is fed to the calibrating means 37. Therein, the corrected time-integrated absorbance value is multiplied by the calibration factor which is selected to produce the result of the determination o the analyte at the display unit 39 in mass units, concentration units or any other desirable units.

When carrying out a greater number of such determinations using samples containing increasing amount of the analyte, there is obtained a substantially linear calibration graph as will be evident from the following Examples.

The Examples were investigated using a Perkin-Elmer PE 5000 Zeeman spectrometer equipped with a standard HGA 500 graphite tube atomizer operating according to the stabilized temperature platform technique. Each one of the analytes was dissolved in 0.5% aqueous nitric acid; sample volumes were in the range of 5 to 30 $\mu$l and the amounts were as plotted on the abscissae. On the ordinates are plotted time-integrated absorbance values.

Figure 2:
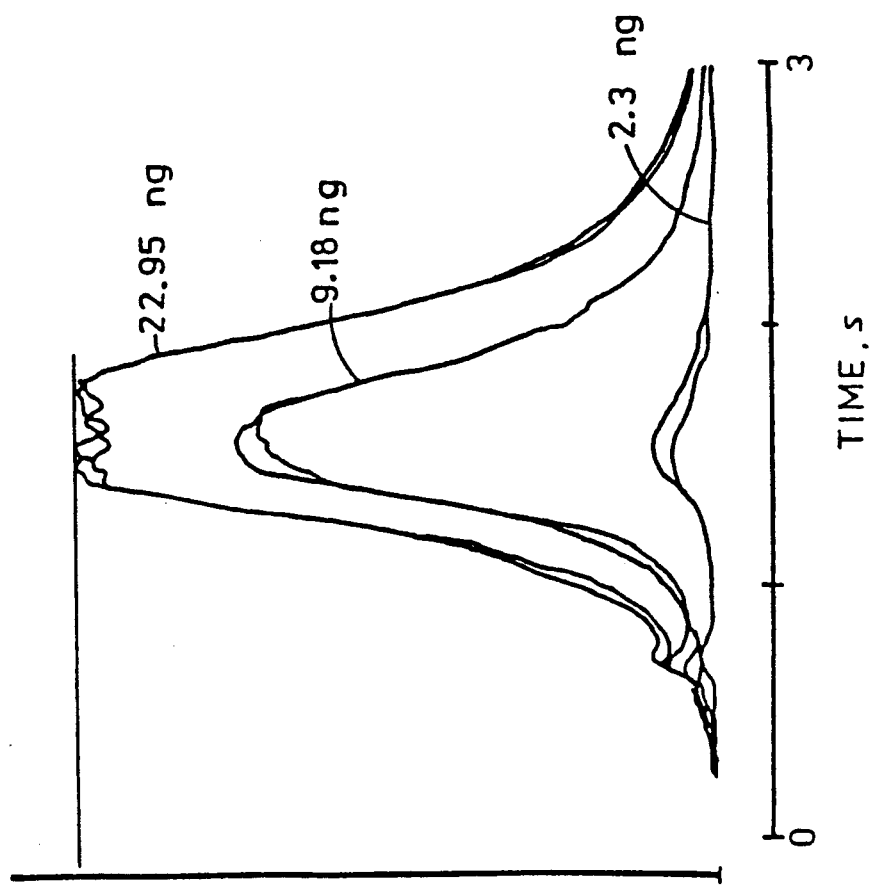
FIG. 2 is a graphic diagram showing transient atomic absorption signals obtained for three different amounts of bismuth as a function of time.
Figure 3:
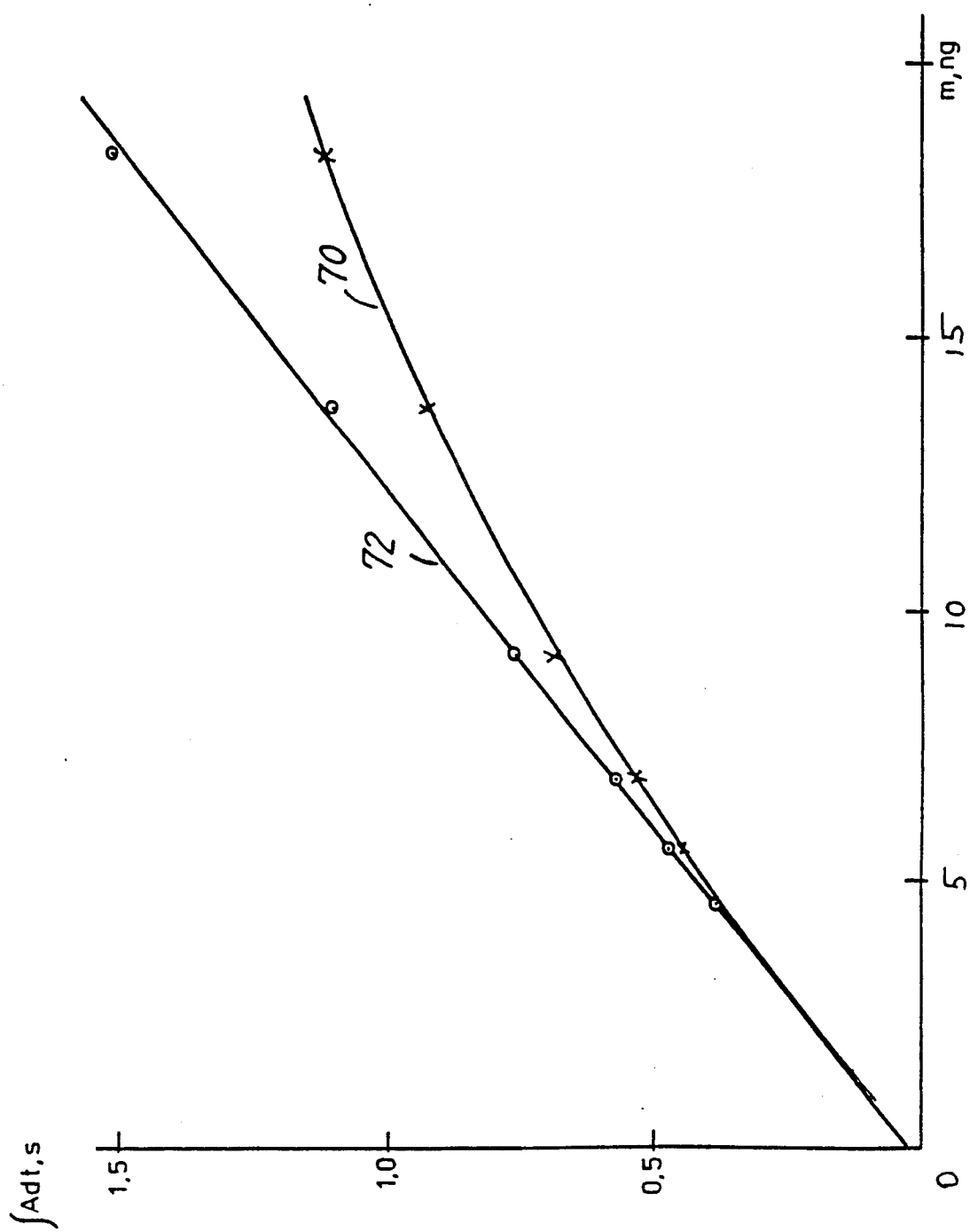
FIG. 3 is a graphic diagram showing the time-integrated absorbance as a function of the amount of bismuth, curve 70 representing a conventional non-corrected calibration curve and linear graph 72 representing the linear calibration graph obtained using the atomic absorption spectrophotometer illustrated in FIG. 1.

FIG. 2 shows the transient absorption signals obtained when subjecting three different amounts of bismuth to atomization in the aforenoted instrument. FIG. 3 shows a conventional calibration curve 70 showing the non-corrected time-integrated absorbance $\int A dt$,s as a function of the mass m in ng of bismuth introduced into the electrothermal atomizing means 16; the linear calibration graph 72 shows the time-integrated absorbance $\int A dt$,s corrected in accordance with the first exemplary embodiment of the invention, as a function of the mass m in ng of bismuth introduced into the electrothermal atomizing means 16.

Figure 4:
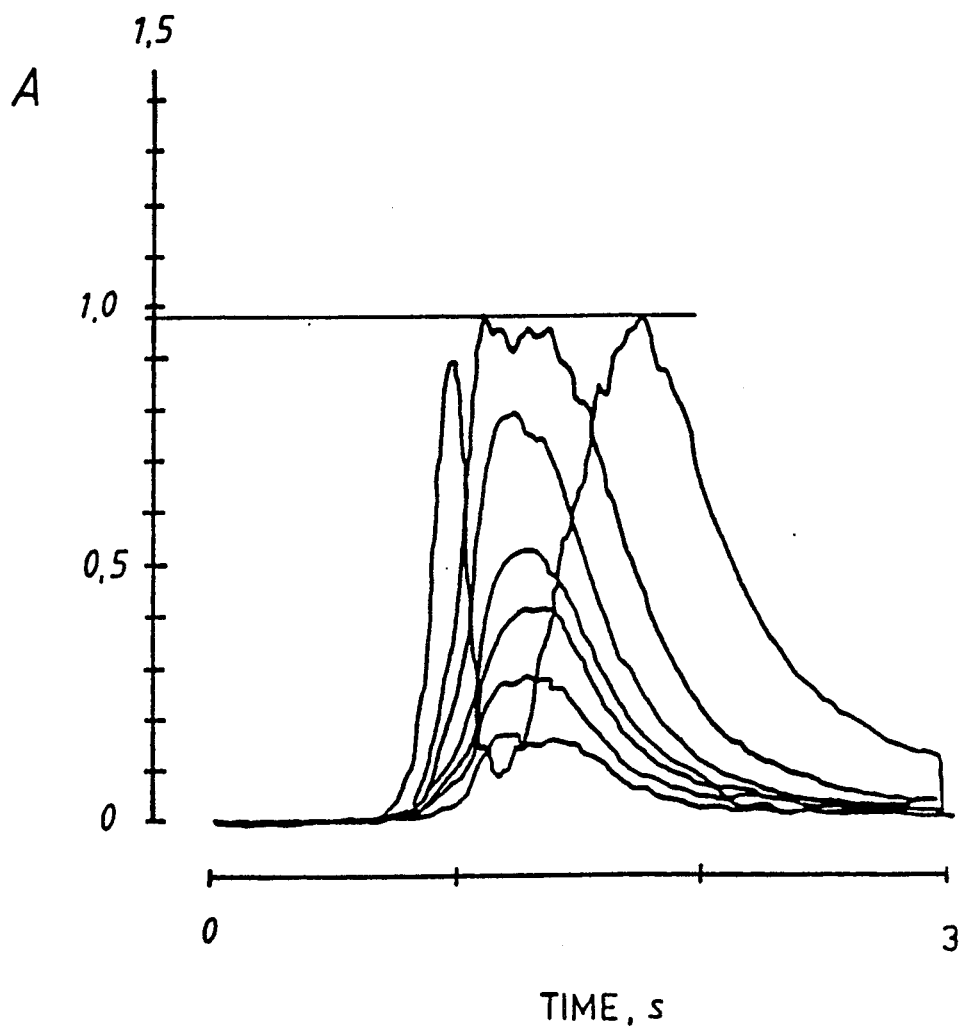
FIG. 4 is a graphic diagram showing transient atomic absorption signals obtained for seven different amounts of gallium as a function of time.
Figure 5:
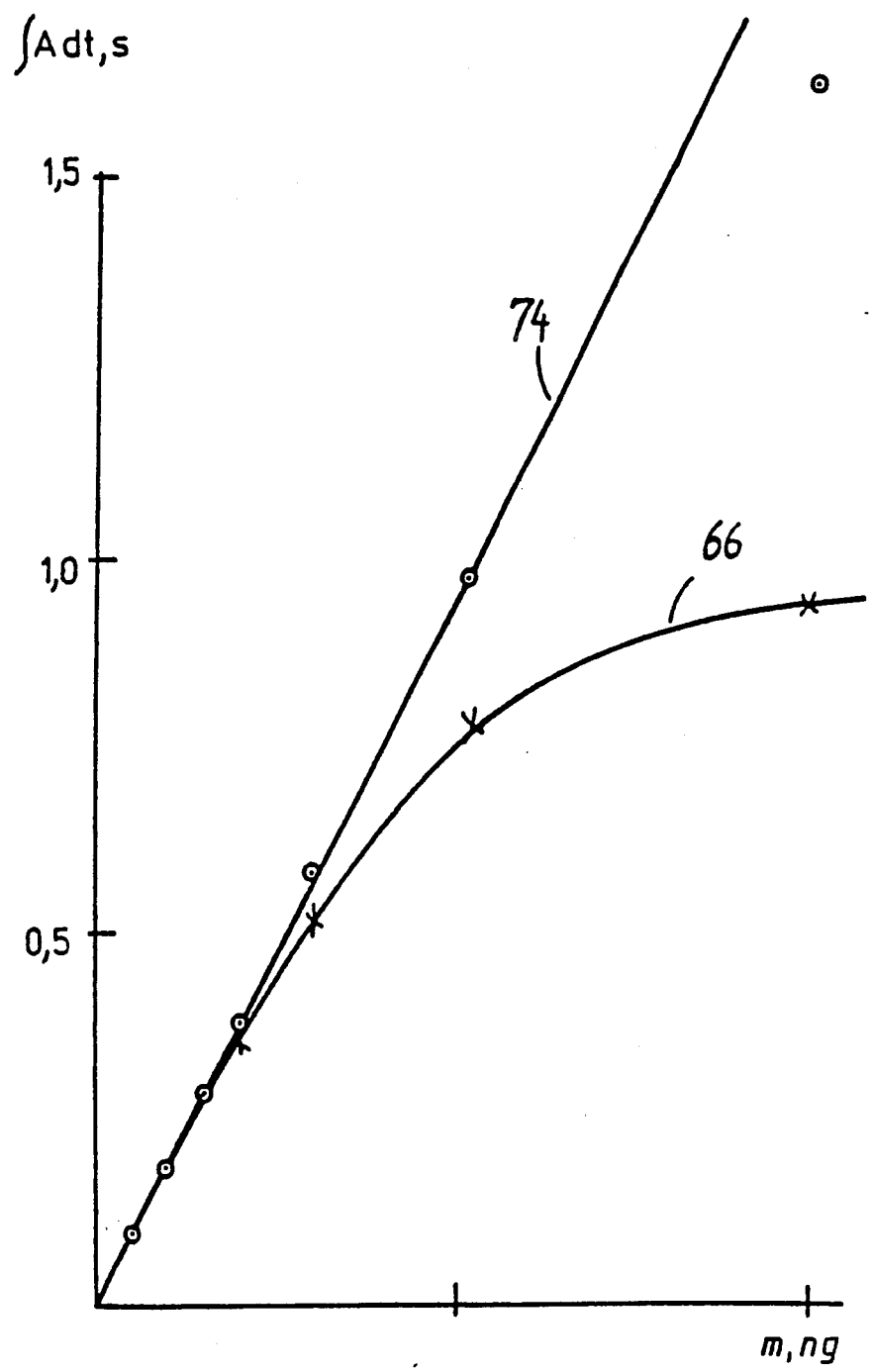
FIG. 5 is a graphic diagram showing the time-integrated absorbance as a function of the amount of gallium, curve 66 representing a conventional non-corrected calibration curve and linear graph 74 representing the linear calibration graph obtained using the atomic absorption spectrophotometer illustrated in FIG. 1.

FIG. 4 shows the transient absorption signals obtained when subjecting seven different amounts of gallium to atomization in the aforenoted instrument. FIG. 5 shows a conventional calibration curve 66 showing the non-corrected time-integrated absorbance $\int A dt$,s as a function of the mass m in ng of gallium introduced into the electrothermal atomizing means 16; the linear calibration graph 74 shows the time-integrated absorbance $\int A dt$,s corrected in accordance with the first exemplary embodiment of the invention, as a function of the mass m in ng of gallium introduced into the electrothermal atomizing means 16.

Figure 6:
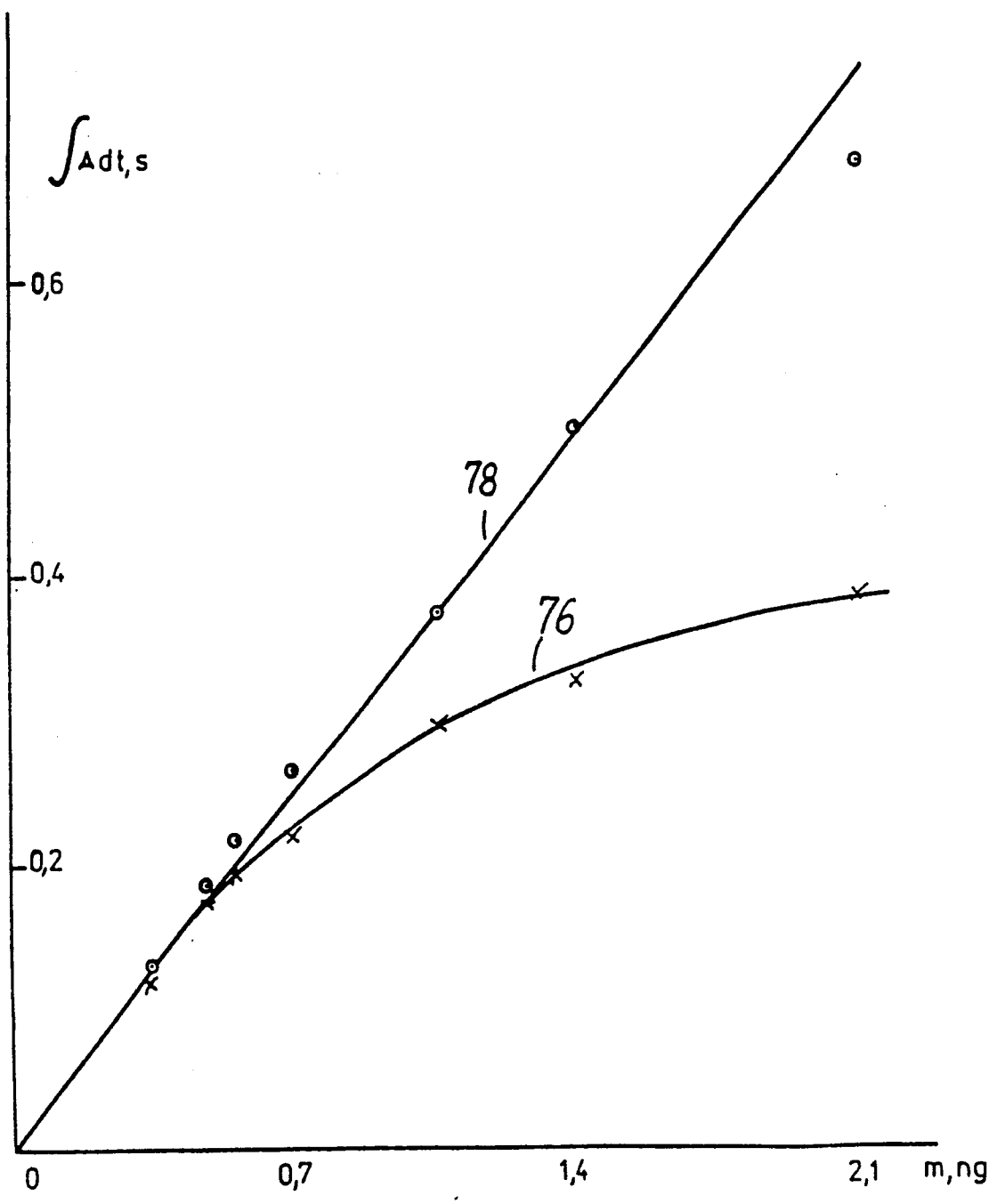
FIG. 6 is a graphic diagram showing the time-integrated absorbance as a function of the amount of gold, curve 76 representing a conventional non-corrected calibration curve and linear graph 78 representing the linear calibration graph obtained using the atomic absorption spectrophotometer illustrated in FIG. 1.

FIG. 6 shows a conventional calibration curve 76 showing the non-corrected time-integrated absorbance $\int A dt$,s as a function of the mass m in ng of gold introduced into the electrothermal atomizing means 16; the linear calibration graph 78 shows the time-integrated absorbance $\int A dt$,s corrected in accordance with the first exemplary embodiment of the invention, as a function of the mass m in ng of gold introduced into the electrothermal atomizing means 16.

Figure 7:
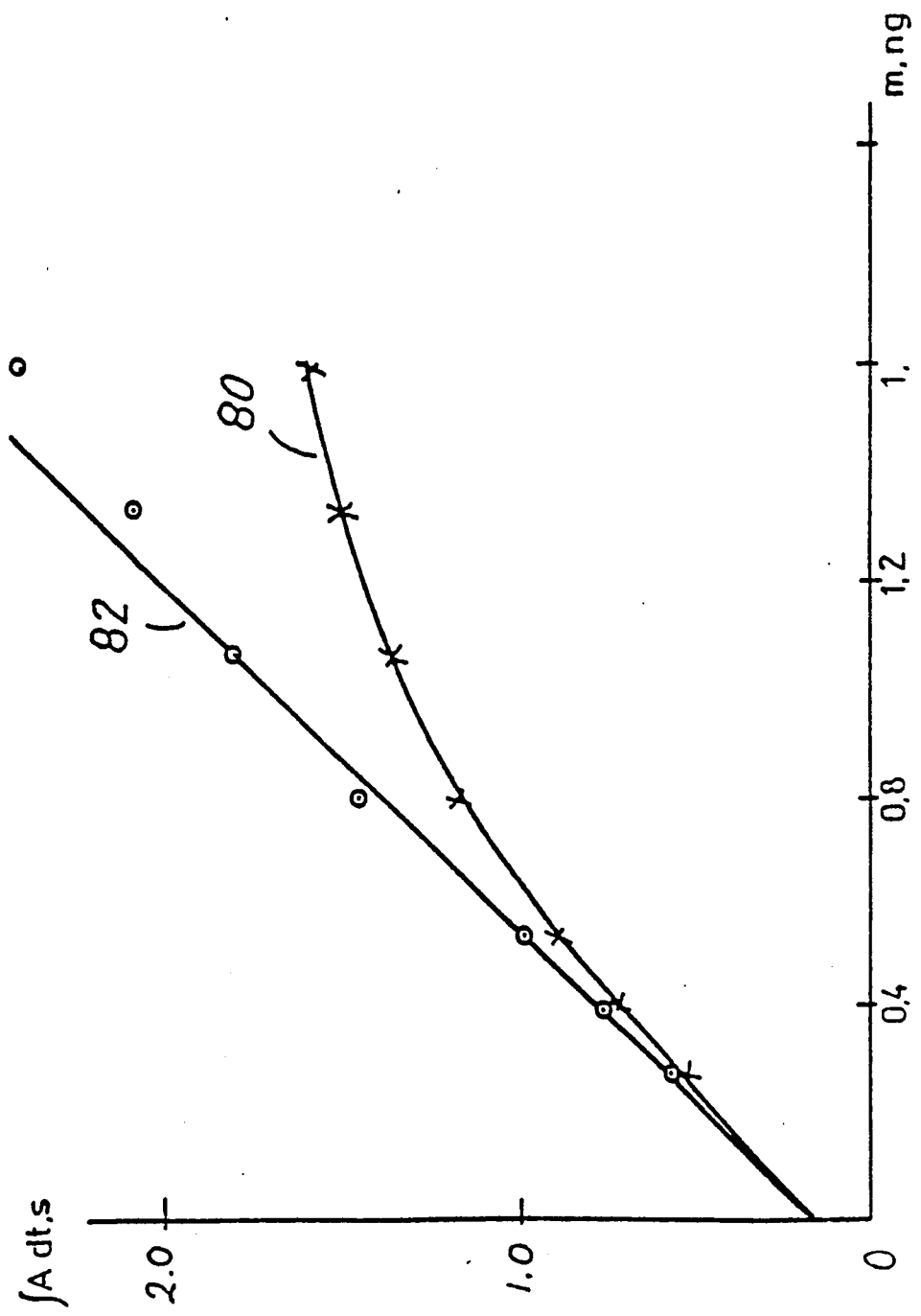
FIG. 7 is a graphic diagram showing the time-integrated absorbance as a function of the amount of silver, curve 80 representing a conventional non-corrected calibration curve and linear graph 82 representing the linear calibration graph obtained using the atomic absorption spectrophotometer illustrated in FIG. 1.

FIG. 7 shows a conventional calibration curve 80 showing the non-corrected time-integrated absorbance $\int A dt$,s as a function of the mass m in ng of silver introduced into the electrothermal atomizing means 16; the linear calibration graph 82 shows the time-integrated absorbance $\int A dt$,s corrected in accordance with the first exemplary embodiment of the invention, as a function of the mass m in ng of silver instroduced into the electrothermal atomizing means 16.

Figure 8:
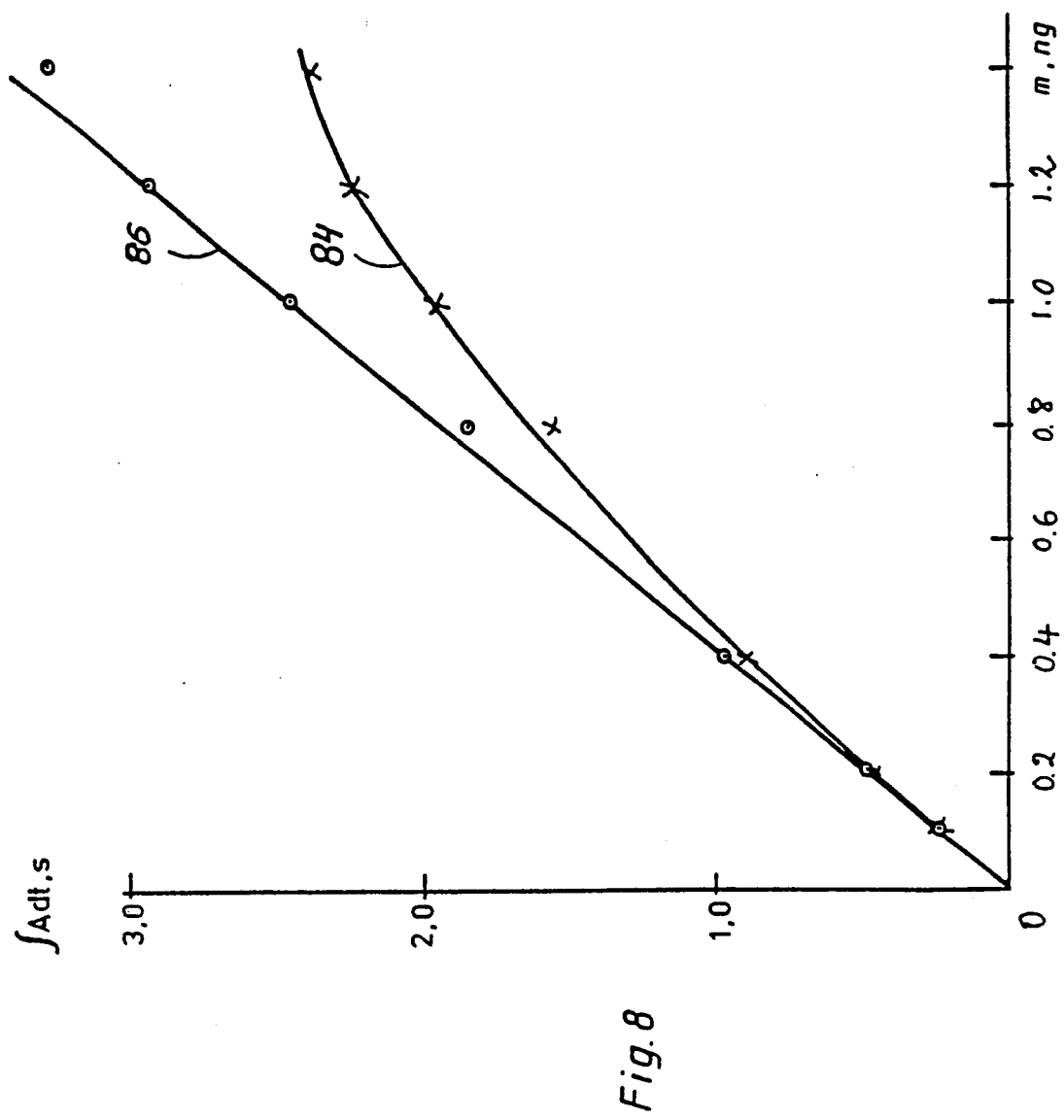
FIG. 8 is a graphic diagram showing the time-integrated absorbance as a function of the amount of copper, curve 84 representing a conventional non-corrected calibration curve und linear graph 86 representing the linear calibration graph obtained using the atomic absorption spectrophotometer illustrated in FIG. 1.

FIG. 8 shows a conventional calibration curve 84 showing the non-corrected time-integrated absorbance ∫Adt,s as a function of the mass m in ng of copper introduced into the electrothermal atomizing means 16; the linear calibration graph 86 shows the time-integrated absorbance ∫Adt,s corrected in accordance with the first exemplary embodiment of the invention, as a function of the mass m in ng of copper instroduced into the electrothermal atomizing means 16.

Figure 9:
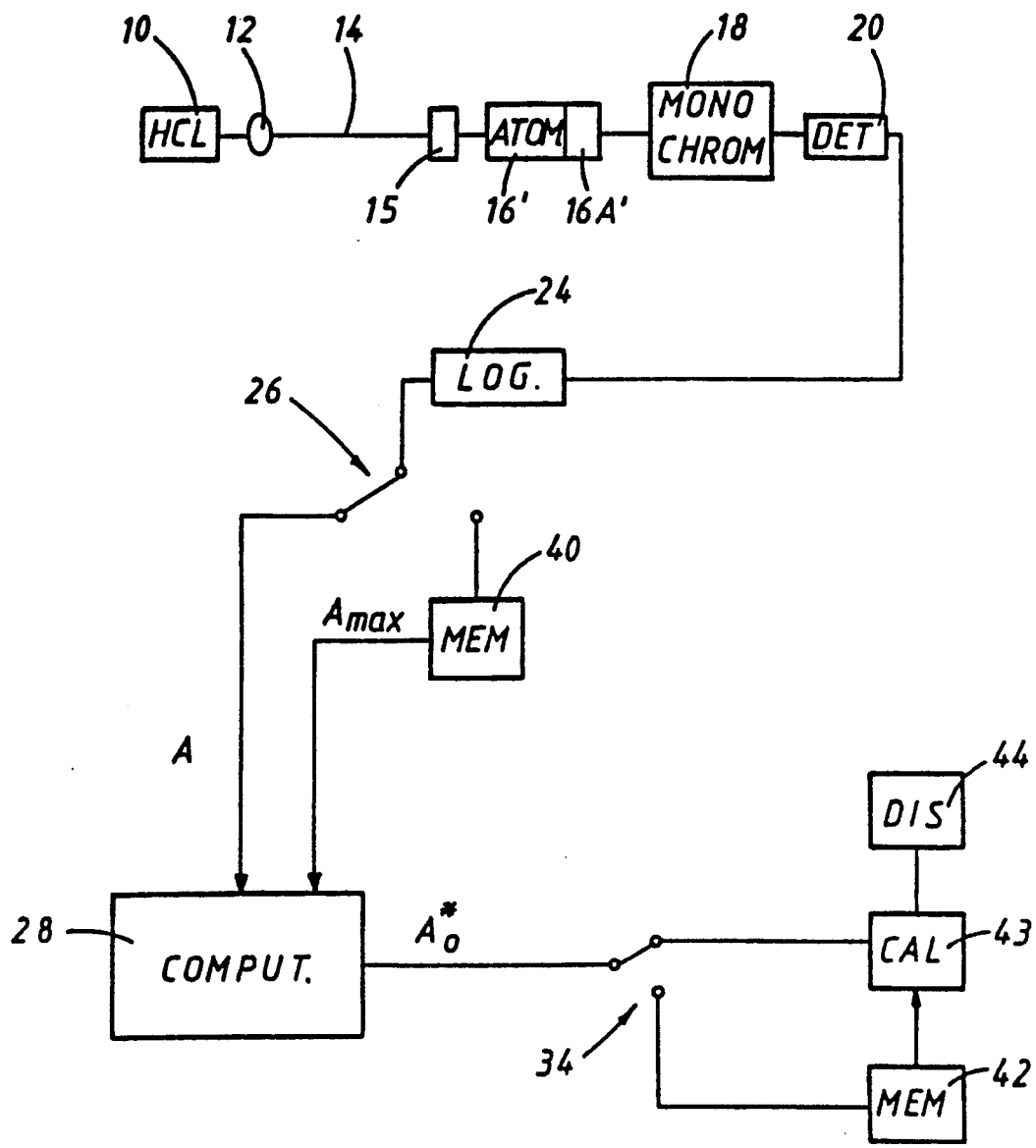
FIG. 9 is a block diagram illustrating a second exemplary embodiment of the inventive atomic absorption spectrophotometer.

A second exemplary embodiment of the inventive atomic absorption spectrophotometer is illustrated in FIG. 9 of the drawings. This embodiment is of a simplified construction and can be used in all cases in which measurement of the peak height is sufficiently precise; other than electrothermal atomizing means like, for example, flame atomizers can be employed. The basic construction of this embodiment is the same as that of the first embodiment illustrated in FIG. 1, i.e. there are present the hollow cathode lamp 10, the optical system 12, the modulating means 15, atomizing means 16' defining an atomic vapor area 16A', the monochromator 18, the detector means 20, and the logarithmating means 24. Zeeman background correcting means are not shown, but may also be present, if desired.

The applying means 26 selectively connect the logarithmating means 24 to either one of the programmable computing means 28 or first memory means 40. Second applying means 34 selectively connect the programmable computing means 28 on its output side to either one of second memory means 42 or calibrating means 43. The calibrating means 43, in turn, are connected on their input side to the second memory means 42 and, on its output side, to a display unit 44 such as a recorder, screen or the like. The programmable computing means 28 likewise may be part of or incorporated into the central data processing and control unit of the atomic absorption spectrophotometer.

The second embodiment operates as follows:

At first, a sample containing the analyte to be determined in a high amount in the range in which the peak height absorbance changes only little as a function of the amount of the analyte, is introduced into and atomized in the atomizing means 16'. The first applying means 26 is adjusted for connecting the logarithmating means 24 to the first memory means 40. The peak height absorbance value thus obtained is stored in the first memory means 40 as the maximum absorbance value $A_{max}$.

Then, the first applying means 26 is switched for connecting the logarithmating means 24 to the programmable computing means 28 and the second applying means 34 is adjusted such as to interconnect the programmable computing means 28 and the second memory means 42. A calibration sample containing a known amount of the analyte to be determined, is introduced into and atomized in the atomizing means 16'. The programmable computing means 28, then, receives the peak height absorbance value A produced by the calibration sample and is programmed to correct this value as a function of the maximum absorbance value $A_{max}$, most preferably in accordance with the function $$A_o^* = (1 - 10^{-A_{max}})\log \frac{10^{A_{max}} - 1}{10^{A_{max}-A} - 1}$$

as given in equation (7) hereinabove. The thus obtained corrected peak height absorbance value is fed to and stored in the second memory means 42.

Thereafter, the second applying means 34 is switched for connecting the programmable computing means 28 to the calibrating means 43. The stored corrected peak height absorbance value, which is associated with the calibration sample and present in the second memory means 42, is transferred to the calibrating means 43 which forms a calibration factor on the basis of the corrected peak height absorbance value and the known amount of the analyte contained in the calibration sample. A sample containing an unknown amount of the analyte, is introduced into and atomized in the atomizing means 16'. The programmable computing means 28, then, processes the incoming peak height absorbance value as a function of the maximum absorbance value which is transferred from the first memory means 40, most preferably in accordance with the function $$A_o^* = (1 - 10^{-A_{max}})\log \frac{10^{A_{max}} - 1}{10^{A_{max}-A} - 1}$$

as given in equation (7) hereinabove. The thus obtained corrected peak height absorbance value is fed to the calibrating means 43. Therein, the corrected peak height absorbance value is multiplied by the calibration factor which is selected to produce the result of the determination of the analyte at the display unit 44 in mass units, concentration units or any other desirable units.

When carrying out a greater number of such determinations using samples containing increasing amounts of the analyte, there is obtained a substantially linear calibration graph as will be evident from the following Example.

Figure 10:
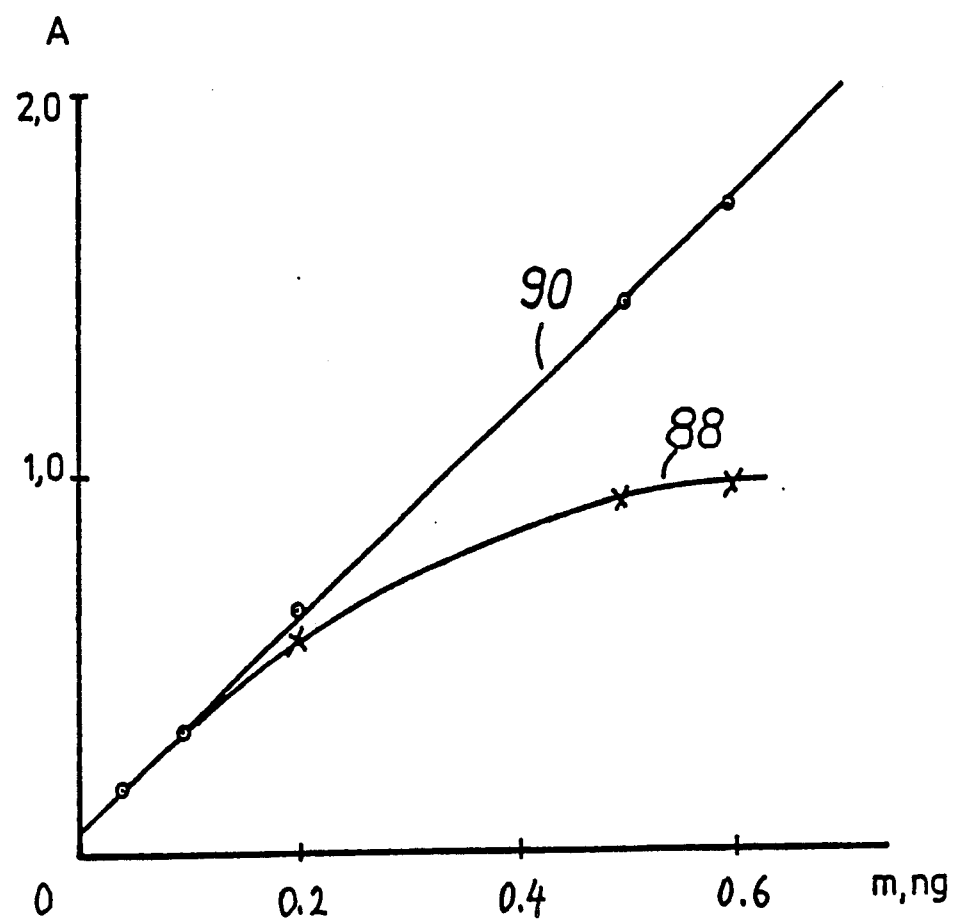
FIG. 10 is a graphic diagram showing the time-integrated absorbance as a function of the amount of cadmium, curve 88 representing a conventional non-corrected calibration curve und linear graph 90 representing the linear calibration graph obtained using the atomic absorption spectrophotometer illustrated in FIG. 9.

Various amounts of cadmium were dissolved and analyzed in substantially the same manner as the Examples given hereinbefore. FIG. 10 shows the results, namely a conventional calibration curve 88 showing the non-corrected peak height absorbance A as a function of the mass m in ng of cadmium introduced into the atomizing means 16'; the linear graph 90 shows the peak height absorbance A corrected in accordance with the second exemplary embodiment of the invention, as a function of the mass m in ng of cadmium introduced into the atomizing means 16'.

What is claimed is:

1. A method of determining by atomic absorption the amount of an analyte contained in a sample, comprising the steps of:

electrothermally atomizing a predetermined number of samples containing known amounts of an analyte and integrating with respect to time the respectively obtained transient atomic absorption signals and thereby determining a maximum absorbance value;

electrothermally atomizing the sample containing an unknown amount of said analyte and thereby obtaining a transient atomic absorption signal composed of individual absorbance values as a function of time;

evaluating said individual absorbance values as a function of said maximum absorbance value and thereby obtaining corrected individual absorbance values;

integrating said corrected individual absorbance values with respect to time and thereby producing a corrected time-integrated absorbance value which is proportional to said unknown amount of said analyte contained in said sample, said step of integrating said corrected individual absorbance values and thereby producing said corrected time-integrated absorbance value including producing a time-integrated absorbance value which is substantially corrected for stray light effects;

determining a calibration factor; and determining said unknown amount of said analyte contained in said sample from said corrected time-integrated absorbance value and said calibration factor.

2. The method according to claim 1, wherein said steps of electrothermally atomizing a predetermined number of samples and determining said maximum absorbance value entails selecting, as said predetermined number of samples, a sample containing an amount of analyte in a range where the absorbance value varies only little with the amount of analyte contained in the sample and using the thus obtained absorbance value as said maximum absorbance value.

3. A method of determining by atomic absorption the amount of an analyte contained in a sample, comprising the steps of:

electrothermally atomizing a predetermined number of samples containing known amounts of an analyte and integrating with respect to time the respectively obtained transient atomic absorption signals and thereby determining a maximum absorbance value;

electrothermally atomizing the sample containing an unknown amount of said analyte and thereby obtaining a transient atomic absorption signal composed of individual absorbance values as a function of time;

evaluating said individual absorbance values as a function of said maximum absorbance value and thereby obtaining corrected individual absorbance values, said step of evaluating said individual absorbance values as a function of said maximum absorbance value entailing evaluating said individual absorbance values in accordance with the function $$A_o^* = (1 - 10^{-A_{max}})\log \frac{10^{A_{max}} - 1}{10^{A_{max}-A} - 1}$$

wherein $A_o^*$ is corrected individual absorbance value, $A_{max}$ is the maximum absorbance value, and A is the individual absorbance value;

integrating said corrected individual absorbance values with respect to time and thereby producing a corrected time-integrated absorbance value which is proportional to said unknown amount of said analyte contained in said sample;

determining a calibration factor; and determining said unknown amount of said analyte contained in said sample from said corrected time-integrated absorbance value and said calibration factor.

4. A method of determining by atomic absorption the amount of an analyte contained in a sample, comprising the steps of:

electrothermally atomizing a predetermined number of samples containing known amounts of an analyte and integrating with respect to time the respectively obtained transient atomic absorption signals and thereby determining a maximum absorbance value;

electrothermally atomizing the sample containing an unknown amount of said analyte and thereby obtaining a transient atomic absorption signal composed of individual absorbance values as a function of time;

evaluating said individual absorbance values as a function of said maximum absorbance value and thereby obtaining corrected individual absorbance values;

integrating said corrected individual absorbance values with respect to time and thereby producing a corrected time-integrated absorbance value which is proportional to said unknown amount of said analyte contained in said sample, determining a calibration factor; said step of determining said calibration factor entailing the following steps:

electrothermally atomizing a calibration sample containing a known amount of said analyte and thereby obtaining a transient atomic absorption signal composed of individual absorbance values as a function of time;

evaluating said individual absorbance values as a function of said maximum absorbance value and thereby obtaining corrected individual absorbance values;

integrating said corrected individual absorbance values with respect to time and thereby producing a corrected time-integrated absorbance value which is proportional to said known amount of said analyte contained in said calibration sample; and determining said calibration factor from said corrected time-integrated absorbance value and said known amount of analyte contained in said calibration sample; and determining said unknown amount of said analyte contained in said sample from said corrected time-integrated absorbance value and said calibration factor.

5. A method of determining by atomic absorption the amount of an analyte contained in a sample, comprising the steps of:

electrothermally atomizing a predetermined number of samples containing known amounts of an analyte and integrating with respect to time the respectively obtained transient atomic absorption signals and thereby determining a maximum absorbance value;

electrothermally atomizing the sample containing an unknown amount of said analyte and thereby obtaining a transient atomic absorption signal composed of individual absorbance values as a function of time;

evaluating said individual absorbance values as a function of said maximum absorbance value and thereby obtaining corrected individual absorbance values; said step of evaluating said individual absorbance values as a function of said maximum absorbance value entailing evaluating said individual absorbance values in accordance with the function $$A_o^* = (1 - 10^{-A_{max}})\log\frac{10^{A_{max}} - 1}{10^{A_{max}-A} - 1}$$

wherein
$A_o^*$ is the corrected individual absorbance value,
$A_{max}$ is the maximum absorbance value, and
$A$ is the individual absorbance value;
integrating said corrected individual absorbance values with respect to time and thereby producing a corrected time-integrated absorbance value which is proportional to said unknown amount of said analyte contained in said sample;
determining a calibration factor; and
determining said unknown amount of said analyte contained in said sample from said corrected time-integrated absorbance value and said calibration factor.

6. A method of determining by atomic absorption the amount of an analyte contained in a sample, comprising the steps of:
atomizing a sample containing a known high amount of an analyte and determining a maximum absorbance value as the peak height of the thus obtained transient atomic absorption signal;
atomizing the sample containing an unknown amount of said analyte and determining a peak height absorbance value as the peak height of the thus obtained transient atomic absorption signal;
evaluating said peak height absorbance value as a function of said maximum absorbance value and thereby obtaining a corrected peak height absorbance value which is proportional to said unknown amount of said analyte contained in said sample, said step of evaluating said peak height absorbance value as a function of said maximum absorbance value and thereby obtaining said corrected peak height absorbance value including producing a peak height absorbance value which is substantially corrected for stray light effects;
determining a calibration factor; and
determining said unknown amount of said analyte contained in said sample from said corrected peak height absorbance value and said calibration factor.

7. The method according to claim 6, wherein said steps of electrothermally atomizing said sample containing said high amount of said analyte and determining said maximum absorbance value entails selecting, as said sample, a sample containing an amount of analyte in a range where the peak height absorbance value varies only little with the amount of analyte contained in the sample and using the thus obtained peak height absorbance value as said maximum absorbance value.

8. A method of determining by atomic absorption the amount of an analyte contained in a sample, comprising the steps of:
atomizing a sample containing a known high amount of an analyte and determining a maximum absorbance value as the peak height of the thus obtained transient atomic absorption signal;
atomizing the sample containing an unknown amount of said analyte and determining a peak height absorbance value as the peak height of the thus obtained transient atomic absorption signal;
evaluating said peak height absorbance value as a function of said maximum absorbance value and thereby obtaining a corrected peak height absorbance value which is proportional to said unknown amount of said analyte contained in said sample;
said step of evaluating said peak height absorbance value as a function of said maximum absorbance value entailing evaluating said peak height absorbance value in accordance with the function $$A_o^* = (1 - 10^{-A_{max}})\log\frac{10^{A_{max}} - 1}{10^{A_{max}-A} - 1}$$

wherein
$A_o^*$ is the corrected peak height absorbance value,
$A_{max}$ is the maximum absorbance value, and
$A$ is the peak height absorbance value;
determining a calibration factor; and
determining said unknown amount of said analyte contained in said sample from said corrected peak height absorbance value and said calibration factor.

9. A method of determining by atomic absorption the amount of an analyte contained in a sample, comprising the steps of:
atomizing the sample containing a known high amount of an analyte and determining a maximum absorbance value as the peak height of the thus obtained transient atomic absorption signal; said steps of atomizing said sample containing said high amount of said analyte and determining said maximum absorbance value entailing selecting, as said sample, a sample containing an amount of analyte in a range where the peak height absorbance value varies only little with the amount of analyte contained in the sample and using the thus obtained peak height absorbance value as said maximum absorbance value;
atomizing a sample containing an unknown amount of said analyte and determining a peak height absorbance value as the peak height of the thus obtained transient atomic absorption signal;
evaluating said peak height absorbance value as a function of said maximum absorbance value and thereby obtaining a corrected peak height absorbance value which is proportional to said unknown amount of said analyte contained in said sample;
determining a calibration factor; said step of determining said calibration factor entailing the following steps:
atomizing a calibration sample containing a known amount of said analyte and determining a peak height absorbance value as the peak height of the thus obtained transient atomic absorption signal;
evaluating said peak height absorbance value as a function of said maximum absorbance value and thereby obtaining a corrected peak height absorbance value which is proportional to said known amount of said analyte contained in said calibration sample; and
determining said calibration factor from said corrected peak height absorbance value and said known amount of analyte contained in said calibration sample; and determining said unknown amount of said analyte contained in said sample from said corrected peak height absorbance value and said calibration factor.

10. The method as defined in claim 9, wherein said step of evaluating said peak height absorbance value as a function of said maximum absorbance value entails evaluating said peak height absorbance value in accordance with the function $$A_o^* = (1 - 10^{-A_{max}}) \log \frac{10^{A_{max}} - 1}{10^{A_{max}-A} - 1}$$

wherein $A_o^*$ is the corrected peak height absorbance value,
$A_{max}$ is the maximum absorbance value, and
A is the peak height absorbance value.

11. An atomic absorption spectrophotometer for determining the amount of an analyte contained in a sample, comprising:

line emitting light source means for emitting a measuring light beam containing a resonance line of an analyte contained in a sample;

electrothermal atomizing means for receiving said sample and atomizing said sample;

said electrothermal atomizing means defining an atomic vapor area for forming the atomized sample;

said atomizing means being arranged for passing said measuring light beam emitted by said line emitting light source means through said atomic vapor area of said electrothermal atomizing means;

detector means arranged for receiving said measuring light beam after passage through said atomic vapor area of said electrothermal atomizing means;

modulating means for alternatingly passing said measuring light beam through said atomic vapor area of said atomizing means to said detector means and to said detector means for producing alternating detector output signals respectively indicative of an attenuated light intensity, which is attenuated due to absorption of the measuring light beam by the atomized sample in said atomic vapor area of said electrothermal atomizing means, and of a reference light intensity;

logarithmating means connected to said detector means for receiving said alternating detector output signals and forming therefrom a logarithmic ratio signal representative of an absorbance value;

said atomized sample being transiently formed in said atomic vapor area of said electrothermal atomizing means and said detector means generating a correspondingly transient atomic absorption signal which is transformed by said logarithmating means into individual absorbance values as a function of time;

integrating means selectively connected to said logarithmating means for receiving therefrom said individual absorbance values and forming a time-integrated absorbance value;

first memory means for storing a maximum absorbance value obtained from a sample containing a predetermined high amount of said analyte;

programmable computing means for computing corrected absorbance values which are proportional to the amount of analyte contained in the sample;

first applying means for selectively connecting said logarithmating means to said integrating means and to said computing means;

said first applying means selectively connecting said logarithmating means to said first memory means for storing therein said maximum absorbance value obtained from said sample containing said predetermined high amount of said analyte;

said first memory means being connected to feed said maximum absorbance value to said programmable computing means and said first applying means selectively connecting said logarithmating means to said programmable computing means during atomization of a sample containing an unknown amount of said analyte;

said programmable computing means being programmed to evaluate said individual absorbance values, which are produced by said sample containing said unknown amount of said analyte, as a function of said maximum absorbance value in order to obtain corrected individual absorbance values as a function of time;

said integrating means being selectively connected to receive said corrected individual absorbance values from said programmable computing means in order to produce therefrom a corrected time-integrated absorbance value which is proportional to the unknown amount of said analyte contained in said sample;

calibrating means for generating a calibration factor; and said calibrating means being connected to said integrating means for receiving said corrected time-integrated absorbance values and producing, by means of said calibration factor, an output signal indicative of the amount of said analyte contained in said sample.

12. The atomic absorption spectrophotometer according to claim 11, further including:

Zeeman background correction means;

said electrothermal atomizing means receiving a plural number of samples containing said analyte in known amounts in a range in which the absorbance values pass through a maximum as a function of the amounts contained in said plural number of samples;

said first memory storing, as said maximum absorbance value, the maximum value which is selected from said plural number of said absorbance values.

13. The atomic absorption spectrophotometer according to claim 11, wherein said electrothermal atomizing means receives a sample containing an amount of said analyte in a range in which the absorbance value varies only little with the amount of said analyte contained in said sample, for determining and storing in said first memory means said maximum absorbance value.

14. The atomic absorption spectrophotometer according to claim 11, wherein said programmable computing means is programmed to evaluate said individual absorbance values, which are produced by said sample containing said unknown amount of said analyte, as a function of said maximum absorbance value in order to obtain corrected individual absorbance values substantially corrected for stray light effects.

15. The atomic absorption spectrophotometer according to claim 11, wherein said programmable computing means is programmed to evaluate said individual absorbance values, which are produced by said sample containing said unknown amount of said analyte, in accordance with the following function $$A_o^* = (1 - 10^{-A_{max}})\log \frac{10^{A_{max}} - 1}{10^{A_{max}-A} - 1}$$

wherein
$A_o^*$ is the corrected individual absorbance value,
$A_{max}$ is the maximum absorbance value, and
$A$ is the individual absorbance value.

16. The atomic absorption spectrophotometer according to claim 11, further including:
second memory means;
second applying means for selectively connecting said integrating means to said calibrating means and said second memory means;
said second applying means connecting said integrating means to said second memory means for storing therein a corrected time-integrated absorbance value produced by a calibration sample which is atomized in said electrothermal atomizing means and which contains a known amount of said analyte; and
said calibrating means generating said calibration factor from said corrected time-integrated absorbance value, which is produced by said calibration sample, and said known amount of said analyte present in said calibration sample.

17. The atomic absorption spectrophotometer according to claim 16, wherein said programmable computing means is programmed to evaluate said individual absorbance values, which are produced by said calibration sample containing said known amount of said analyte, in accordance with the following function $$A_o^* = (1 - 10^{-A_{max}})\log \frac{10^{A_{max}} - 1}{10^{A_{max}-A} - 1}$$

wherein
$A_o^*$ is the corrected individual absorbance value,
$A_{max}$ is the maximum absorbance value, and
$A$ is the individual absorbance value.

18. An atomic absorption spectrophotometer for determining the amount of an analyte contained in a sample, comprising:
line emitting light source means for emitting a measuring light beam containing a resonance line of an analyte contained in a sample;
atomizing means for receiving said sample and atomizing said sample;
said atomizing means defining an atomic vapor area for forming the atomized sample;
said atomizing means being arranged for passing said measuring light beam emitted by said line emitting light source means, through said atomic vapor area of said atomizing means; .
detector means arranged for receiving said measuring light beam after passage through said atomic vapor area of said atomizing means;
modulating means for alternatingly passing said measuring light beam through said atomic vapor area of said atomizing means to said detector means and to said detector means for producing alternating detector output signals respectively indicative of an attenuated light intensity, which is attenuated due to absorption of the measuring light beam by the atomized sample in said atomic vapor area of said atomizing means, and of a reference light intensity:
logarithmating means connected to said detector means for receiving said alternating detector output signals and forming therefrom a logarithmic ratio signal representative of an absorbance value;
said atomized sample formed in said atomic vapor area of said atomizing means, producing a detector output signal which is transformed by said logarithmating means into a corresponding peak height absorbance value;
first memory means connected to said logarithmating means for storing a maximum absorbance value obtained from a sample containing a predetermined high amount of said analyte;
programmable computing means for computing corrected peak height absorbance values which are proportional to the amount of said analyte contained in the sample;
first applying means for selectively connecting said logarithmating means to said programmable computing means and to said first memory means;
said programmable computing means being programmed to evaluate a peak height absorbance value, which is produced by a sample containing an unknown amount of said analyte, as a function of said maximum absorbance value in order to obtain a corrected peak height absorbance value;
calibrating means for generating a calibration factor; and
said calibrating means being connected to said programmable computing means for receiving said corrected peak height absorbance value and producing, by means of said calibration factor, an output signal indicative of the amount of said analyte contained in said sample.

19. The atomic absorption spectrophotometer according to claim 18, wherein said atomizing means receives a sample containing an amount of said analyte in a range in which the peak height absorbance value varies only little with the amount of said analyte contained in said sample, for determining and storing in said first memory means said maximum absorbance value.

20. The atomic absorption spectrophotometer according to claim 18, wherein said programmable computing means is programmed to evaluate said peak height absorbance value, which is produced by said sample containing said unknown amount of said analyte, as a function of said maximum absorbance value in order to obtain a corrected peak height absorbance value substantially corrected for stray light effects.

21. The atomic absorption spectrophotometer according to claim 18, wherein said programmable computing means is programmed to evaluate said peak height absorbance value, which is produced by said sample containing said unknown amount of said analyte, in accordance with the following function $$A_o^* = (1 - 10^{-A_{max}})\log \frac{10^{A_{max}} - 1}{10^{A_{max}-A} - 1}$$

wherein
$A_o^*$ is the corrected peak height absorbance value,
$A_{max}$ is the maximum absorbance value, and
$A$ is the peak height absorbance value.

22. The atomic absorption spectrophotometer according to claim 18, further including:

second memory means;
second applying means for selectively connecting said programmable computing means to said calibrating means and said second memory means;
said second applying means connecting said programmable computing means to said second memory means for storing therein a corrected peak height absorbance value produced by a calibration sample which contains a known amount of said analyte and which is atomized in said atomizing means; and
said calibrating means generating said calibrating factor from said corrected peak height absorbance value, which is produced by said calibration sample, and said known amount of said analyte present in said calibration sample.

23. The atomic absorption spectrophotometer according to claim 22, wherein said programmable computing means is programmed to evaluate said peak height absorbance value, which is produced by said calibration sample, in accordance with the following function $$A_o^* = (1 - 10^{-A_{max}})\log \frac{10^{A_{max}} - 1}{10^{A_{max}-A} - 1}$$

wherein
$A_o^*$ is the corrected peak height absorbance value,
$A_{max}$ is the maximum absorbance value, and
A ist the peak height absorbance value.

* * * * *